United States Patent [19]

Kuzma

[11] Patent Number: 4,809,712
[45] Date of Patent: Mar. 7, 1989

[54] ELECTRODE ASSEMBLY FOR COCHLEAR IMPLANT

[75] Inventor: Janusz Kuzma, Kings Langley, Australia

[73] Assignee: Cochlear Pty. Ltd., Lane Cove, Australia

[21] Appl. No.: 912,572

[22] Filed: Sep. 26, 1986

[51] Int. Cl.$^4$ ............................ A61N 1/05; A61N 1/18
[52] U.S. Cl. ................................. 128/784; 128/420.6
[58] Field of Search ................................. 128/784–786, 128/789, 420.6, 304, 419 F; 366/343; 15/104.16

[56] References Cited

U.S. PATENT DOCUMENTS

| 398,258 | 2/1889 | Hudson | 366/343 X |
|---|---|---|---|
| 1,004,786 | 10/1911 | Hess | 366/343 X |
| 2,637,058 | 5/1953 | Anderson | 15/104.16 X |
| 3,416,533 | 12/1968 | Fisher et al. | 128/786 |
| 4,112,952 | 9/1978 | Thomas et al. | 128/785 |
| 4,195,401 | 4/1980 | Galloup | 29/764 |
| 4,284,856 | 8/1981 | Hochmair et al. | 179/107 E |
| 4,333,469 | 6/1982 | Jeffcoat et al. | 128/419 F |
| 4,419,995 | 12/1983 | Hochmair et al. | 128/784 |
| 4,462,401 | 7/1984 | Burgio | 128/785 X |
| 4,462,402 | 6/1984 | Burgio et al. | 128/785 X |
| 4,575,253 | 3/1986 | Kafka | 366/343 X |

OTHER PUBLICATIONS

Hochmair—Desoyer et al, "An Eight Channel Tympani . . . " IEEE Trans Biomed Eng, BME-27, No. 1, Jan. 1980, pp. 44–50.

Primary Examiner—Lee S. Cohen
Attorney, Agent, or Firm—Gottlieb, Rackman & Reisman

[57] ABSTRACT

A cochlear implant electrode assembly and a method for affixing it to a bone in the ear. An electrode ball of unfixed turns is made from one end of each wire leading to the electronics part of the implant, a corresponding attachment hole is drilled in the bone, and the ball is affixed to the hole without the use of fixation devices by tapping the turns into the hole.

14 Claims, 5 Drawing Sheets

ELECTRODE ASSEMBLY FOR COCHLEAR IMPLANT

DESCRIPTION

This invention relates to a cochlear implant, and a method for making a cochlear implant electrode assembly and for affixing that electrode assembly to a bone in the ear, such as the endochondral bone overlaying the cochlea.

The stimulating electrode assembly of a cochlear implant may be placed inside the cochlear partition, commonly into the scala tympani, or in the middle ear against the bone of the inner ear. A major problem with conventional electrode assemblies is in affixing the stimulating electrodes to the surface of the bone in a simple and reliable manner. In the prior art, solid ball electrodes are used, requiring an anchor hole to be drilled to an exact size, the ball to be wedged into the hole, and the use of muscle tissue and/or fibrin glue to affix the ball to the hole securely. Another shortcoming of the prior art is that the solid ball electrodes have to be attached to insulated lead wires. Each such attachment is, by nature, a structural weak point in the electrode assembly.

An object of my invention is to provide an electrode assembly and a technique for electrode attachment which are both simple and reliable and do not require additional fixtures.

In accordance with the principles of my invention, the same wire which acts as an electrode lead is used to make a porous ball electrode. A porous ball is formed from wire which has a filament of small diameter since such wire permits the overall diameter of the ball to be relatively large. Multistranded wire allows easy fabrication of such a porous ball electrode. A length of the wire is stripped and annealed. After cooling, a porous electrode ball is formed by winding turns loosely on a mandrel. (It is the loose winding of unfixed turns which gives rise to the porosity of the ball). There is no structural weak point where the ball electrode is attached to the lead wire because the electrode is made of the same wire. A strong and flexible wire is provided by winding each multistranded wire into a helix and protecting it with a silicone rubber tube which is also back filled with silicone rubber.

A major advantage of my invention is that the method for affixing the electrode ball to the bone does not require a precisely drilled anchor hole or additional fixtures to insure a secure mounting. A hole is drilled in the bone to a depth of approximately 1.3 mm, using a ball-tipped or cylindrical-tipped diamond drill. After the hole is drilled, the electrode ball is affixed to the bone by gradually tapping wire turns from the ball into the hole with a special tool adapted for this purpose. As the ball is pressed into the hole, its density increases, and the ball conforms to the dimensions of the hole. Since the ball conforms to the hole, several different hole shapes are suitable. This contrasts with the prior art, where the anchor hole is required to be of a specific unique shape to accomodate the solid ball electrode. Even with a precisely drilled hole, the solid ball electrode of the prior art requires additional fixtures, such as fibrin glue and/or added muscle tissue, to affix the ball securely to the bone. Since the porous electrode ball of my invention is made to conform to the hole during implantation, no additional fixtures are required. In addition, the porous nature of the ball insures long-term attachment since tissue will grow into the interstices of the ball structure.

Further objects, features and advantages of my invention will become apparent upon consideration of the following detailed description in conjunction with the drawings, in which.

Figure 1:
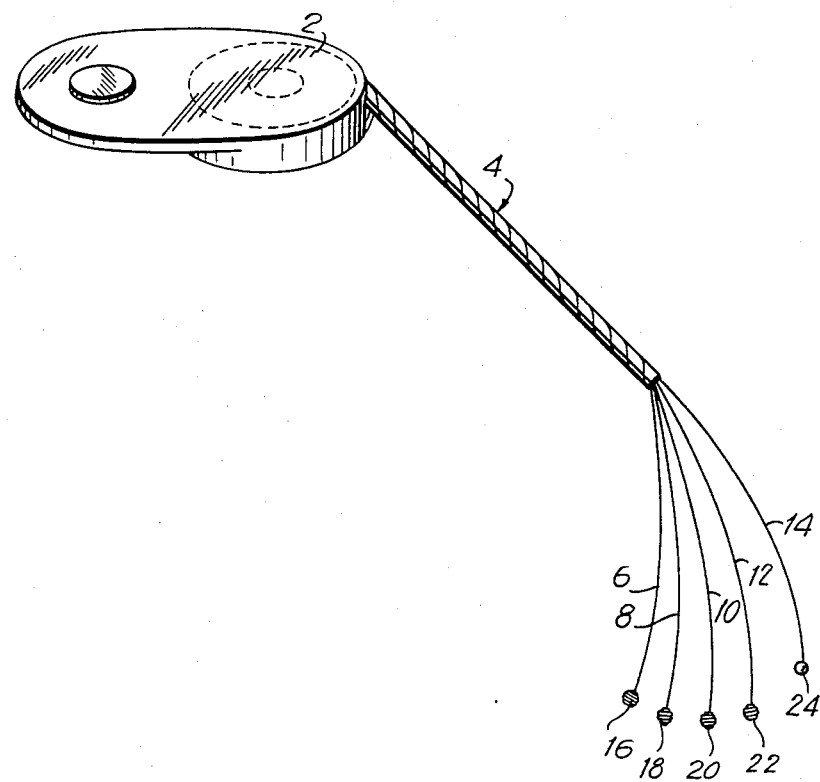
FIG. 1 is a perspective view of the overall implant.

FIG. 1 is an illustration of the overall implant, with an electronics part 2 connected to a 45-mm cable 4. Cable 4 contains Teflon-insulated 9-strand Pt/Ir wires 6, 8, 10, and 12 and Teflon-insulated 11-strand Pt/Ir wire 14, each having a length of 85 mm, 40 mm of which extends out from the cable. (The full length of each wire is actually 125 mm, but 40 mm are used to form the ball electrode). Each lead wire is welded to platinum pins (not shown) on the stimulator 2 (see, e.g., U.S. Pat. No. 4,516,820). Insulated lead wires 6, 8, 10 and 12 terminate in porous electrode balls 16, 18, 20 and 22, and insulated wire 14 terminates in solid ball electrode 24. Electrode balls 16, 18, 20 and 22 each have a diameter of 1.3 mm. Solid ball electrode 24 has a diameter of 1.0 mm.

In the preferred embodiment of the invention, the cochlear implant electrode assembly has four porous electrode balls and one solid electrode ball. A standard intracochlear electrode assembly has twenty-two electrodes, and it is inserted directly into the cochlea. The five-electrode assembly is used where the cochlea has become partially blocked with fibrous tissue or bone, an occurrence in a minority of cases due to the disease which caused the deafness in the first place. Therefore, the five-electrode assembly is attached to the endochondral bone overlaying the cochlea. The solid ball electrode is placed inside one of the scalae of the cochlea through a membrane with a diameter of at least 1.5 mm. A porous ball electrode may also be used, but a solid ball electrode can be packed into the scalae more securely and is preferable. The solid ball electrode is made by melting the end of the electrode lead wire and shaping it.

Since the assembly is implanted further away from the nerves than is a standard cochlear implant, the nerves cannot distinguish pulses from all twenty-two electrodes, and only five electrodes are needed. A soft porous electrode ball provides greater conductivity than a similar diameter solid ball electrode.

Figure 2A:
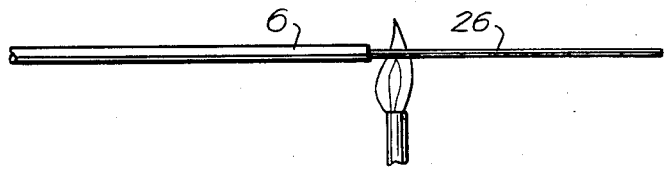
FIG. 2A illustrates stripping and annealing of a 9-strand Teflon-insulated Pt/Ir wire (25 micron diameter)
Figure 2B:
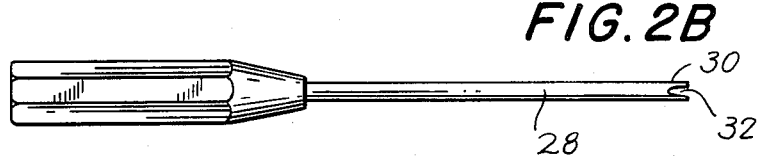
FIG. 2B illustrates a mandrel around which the annealed wire is turned.
Figure 2C:
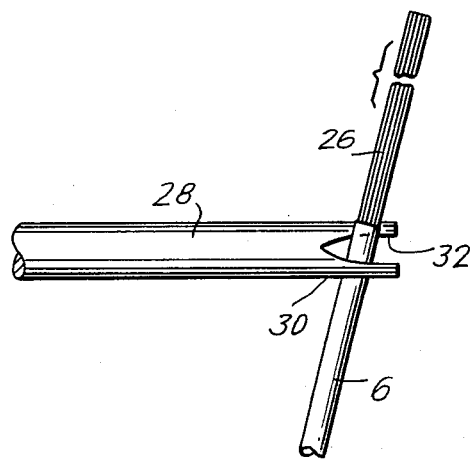
FIGS. 2C–2G illustrate the steps of the preferred method of wrapping the wire around the mandrel.

In FIG. 2A, a 40-mm length 26 of insulated wire 6 is stripped and annealed at a temperature of 1000°–1200° C., after which it is allowed to cool at room temperature. FIG. 2B illustrates the mandrel 28, with a diameter of 0.45 mm, a tip 30 having a length of 1.5 mm and a notch 32 whose width is 0.15 mm. The notch is placed around the end of the remaining insulation 6, as shown in FIG. 2C.

Figure 2D:
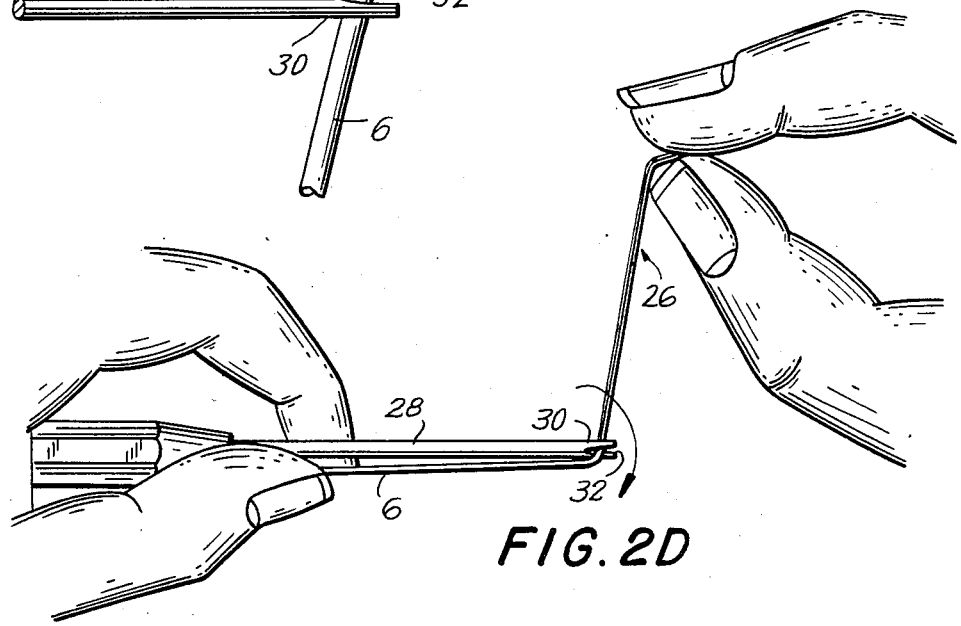
Figure 2E:
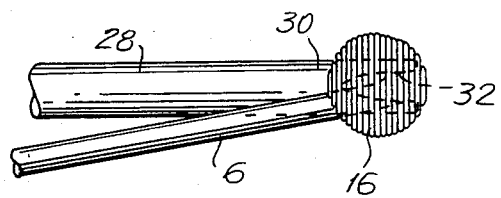
Figure 2F:
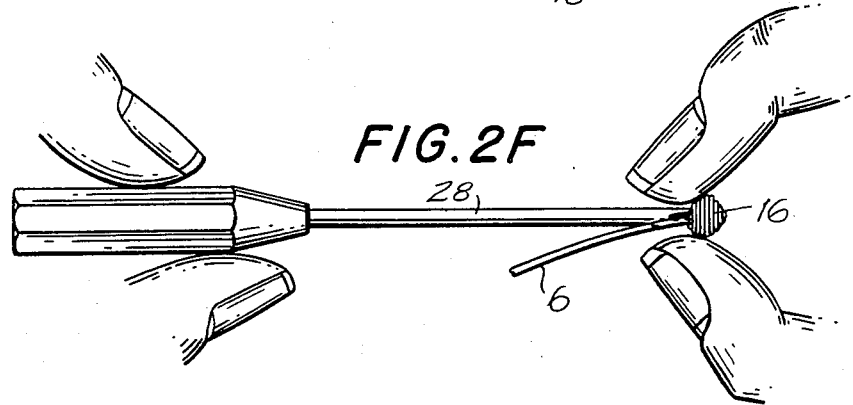
Figure 2G:
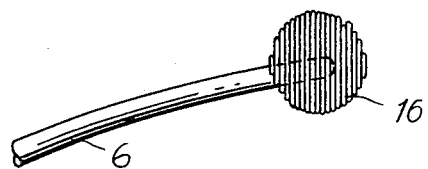
Figure 3:
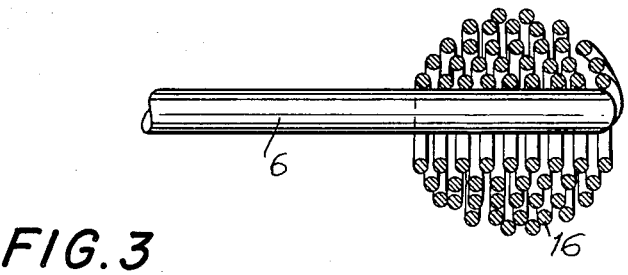
FIG. 3 is an illustration of the cross-section of the electrode ball.

In FIG. 2D, wire 26 is wrapped around mandrel 28 eighteen times to form an electrode ball 16 with unfixed turns and an outer diameter of 1.3 mm, as illustrated in FIG. 2E. In FIG. 2F, mandrel 28 is shown being pulled gently away from electrode ball 16, leaving the electrode ball intact, as shown in FIG. 2G. FIG. 3 illustrates a cross-section of the electrode ball. It is porous in the sense that the winding process leaves spaces between adjacent turns.

Figure 4A:
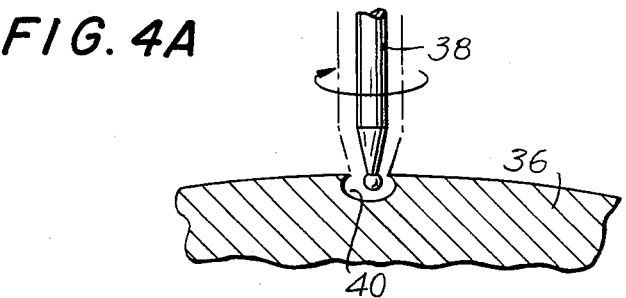
FIG. 4A illustrates the preferred method of drilling the attachment hole.

FIG. 4A illustrates attachment hole 40 in the process of being drilled into endochondral bone 36 by ball-tipped diamond drill 38. The attachment hole has a diameter of 1.0 mm, a dimension substantially smaller than that of the diameter (1.3 mm) of the ball electrode which will be placed in it. In the preferred embodiment, the diameter of the hole is at least 23 percent smaller than the diameter of the ball electrode. The hole is drilled to a depth of about 1.3 mm.

Figure 4B:
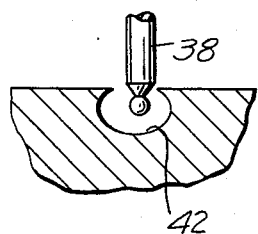
FIGS. 4B–4D are illustrations of preferred shapes of the attachment hole.
Figure 4C:
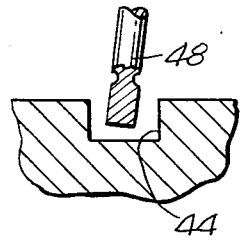
Figure 4D:
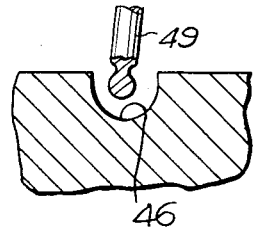

FIG. 4B is an illustration of a finished undercut hole 42 made with the same ball-tipped diamond drill 38. FIG. 4C illustrates a finished square hole 44, made with cylindrical-tipped diamond drill 48. FIG. 4D shows a finished round hole 46, made with a ball-tipped diamond drill 49.

As the hole is drilled and its depth increases, the thickness of bone between the bottom of the hole and underlying fluid-filled space (one of the scalae of the cochlea filled with perilymph fluid) is reduced, and the color of the bone appears to change from white to blue. The hole must not break through into the scalae, so drilling should stop if a "blue line" is seen.

Figure 5A:
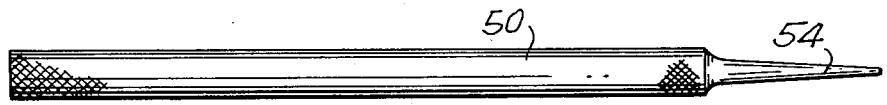
FIGS. 5A and 5B are illustrations of the insertion tool.
Figure 5B:
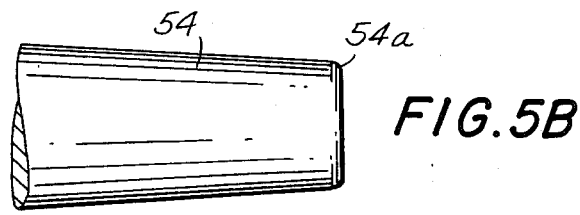

The insertion tool 50 of FIG. 5A has a handle of length 150 mm, and a working end 54 whose length is 40 mm. FIG. 5B, an enlarged view, shows the tip of the working end as having a rounded edge 54a. The diameter of the tip is 0.5 mm.

Figure 6A:
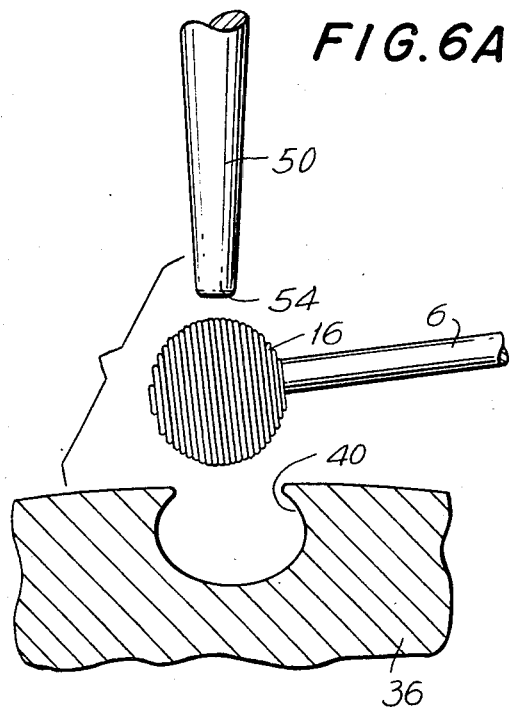
FIGS. 6A–6C illustrate the steps of the preferred method of pressing the electrode ball into the attachment hole.
Figure 6B:
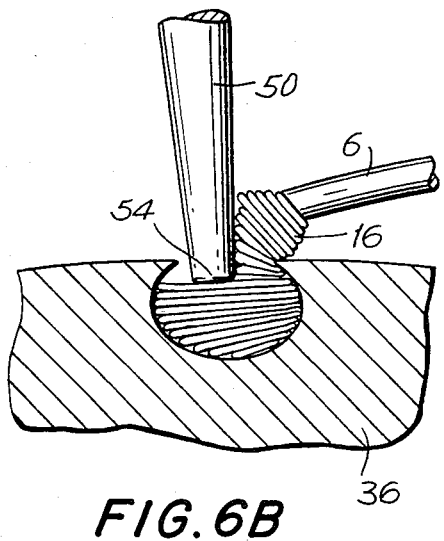
Figure 6C:
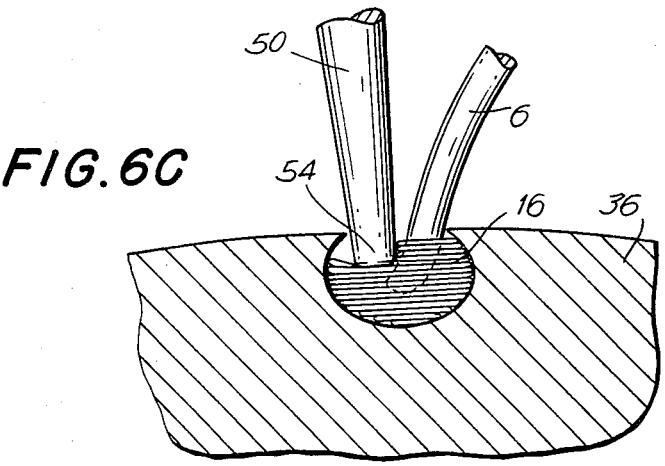

FIGS. 6A-6C illustrate the steps of the preferred method of affixing an electrode ball 16 into attachment hole 40. In FIG. 6A, the electrode ball is positioned directly over the hole, and insertion tool 50 is held vertically over the ball. FIG. 6B illustrates the tip 54 of the insertion tool pressing the electrode ball into hole 40 turn by turn. The pressing or packing process increases the density of the electrode ball and conforms it to the shape of the cavity into which it is placed. In FIG. 6C, the insertion tool has pressed all of the electrode ball in hole 40, with insulated lead wire 6 exiting the hole. Because the lead wire passes into the center of the ball, excellent stress relief is provided.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

I claim:

1. A method of affixing a stimulating electrode to a bone, said stimulating electrode having a plurality of unfixed turns wound in the shape of a ball, comprising the steps of:
   (a) drilling an attachment hole in said bone, said hole having a diameter which is substantially smaller than the diameter of the ball, and
   (b) tapping all of the turns of said ball into said hole.

2. A method of affixing a stimulating electrode to a bone in accordance with claim 1 wherein in step (a) said hole is drilled to a depth of up to but not past the "blue line".

3. A wire for affixation to a bone, a distal end of which is wrapped in the form of a ball filled throughout with unfixed turns in a three-dimensional pattern, said ball being unfilled only at interstices between said turns.

4. A wire in accordance with claim 3, wherein said wire is multistranded.

5. A wire in accordance with claim 3, wherein said ball is in the shape of a sphere.

6. A wire in accordance with claim 3 further comprising, insulation surrounding said wire up to said ball.

7. A wire in accordance with claim 6, wherein said ball is in the shape of a sphere.

8. A wire in accordance with claim 6, wherein said wire is multistranded.

9. A cochlear implant comprising an electronics part for producing pulses for electrical conduction to the ear and a plurality of stimulating electrodes electrically connected to said electronics part and extending therefrom to conduct said pulses, each of said electrodes comprising a wire, a portion of said wire being for affixation directly to a bone, wherein at least one of said wires is wrapped at a distal end thereof in the shape of a ball filled throughout with unfixed turns in a three dimensional pattern, said ball being unfilled only at interstices between said turns, and at least one of said other wires is formed in the shape of a solid ball at a distal end thereof.

10. A cochlear implant in accordance with claim 9, further cmprising insulation surrounding said at least one of said wires said wire is insulated up to said ball.

11. A cochlear implant in accordance with claim 9, wherein said at least one of said other wires is insulated up to said solid ball.

12. A method of affixing a wire to a bone, said wire having a plurality of unfixed turns wound in the shape of a ball, comprising the steps of:
   (a) drilling an attachment hole in said bone, said hole having a dimension which is substantially smaller than a dimension of the ball, and
   (b) tapping all of the turns of said ball into said hole.

13. A method of affixing a wire to a bone in accordance with claim 12 wherein in step (a) said hole is drilled to a depth of up to but not past the "blue line."

14. A method of affixing a wire to a bone in accordance with claim 12, wherein said ball is filled throughout with unfixed turns in a three dimensional pattern, said ball being unfilled only at interstices between said turns.

* * * * *